United States Patent
Williams (10) Patent No.: US 10,499,921 B2
(45) Date of Patent: Dec. 10, 2019

(54) EEA ANVIL SNAP RING ACTIVATOR

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 215 days.

(21) Appl. No.: 15/356,702

(22) Filed: Nov. 21, 2016

(65) Prior Publication Data

US 2017/0065279 A1     Mar. 9, 2017

Related U.S. Application Data (63) Continuation of application No. 13/915,953, filed on Jun. 12, 2013, now Pat. No. 9,532,780.

(51) Int. Cl.
*A61B 17/068* (2006.01)
*A61B 17/115* (2006.01)
*A61B 17/072* (2006.01)

(52) U.S. Cl.
CPC .......... *A61B 17/115* (2013.01); *A61B 17/068* (2013.01); *A61B 17/1155* (2013.01); *A61B 2017/07257* (2013.01)

(58) Field of Classification Search
CPC . A61B 17/115; A61B 17/1155; A61B 17/068; A61B 2017/07257
See application file for complete search history.

(56) References Cited

U.S. PATENT DOCUMENTS

| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |

(Continued)

FOREIGN PATENT DOCUMENTS

| CA | 908529 A | 8/1972 |
| DE | 1057729 B | 5/1959 |

(Continued)

OTHER PUBLICATIONS

Australian Office Action dated Feb. 22, 2018, issued in AU Appln. No. 2014203103.

(Continued)

*Primary Examiner* — Chelsea E Stinson
*Assistant Examiner* — Thomas M Wittenschlaeger (57) ABSTRACT

A surgical fastening apparatus and associated method of use is disclosed. The surgical fastening apparatus includes a handle assembly, a central body portion extending from the handle assembly, and a distal head portion including an anvil head assembly. The anvil head assembly includes an anvil head defining an interior recess, an activator plate, a deformable member, and a securing member. The anvil center rod assembly defines a longitudinal axis and is pivotably connected to the anvil head assembly about a pivot axis. The anvil center rod assembly includes a configured to contact the anvil head assembly upon an actuation of the surgical fastening apparatus. Upon the actuation of the surgical fastening apparatus, the deformable member is configured to deform such that the activator plate is advanced distally into the interior recess to facilitate the anvil head pivoting about the pivot axis.

18 Claims, 10 Drawing Sheets

(56) References Cited

U.S. PATENT DOCUMENTS

| | | |
|---|---|---|
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A * | 12/1996 | Schnut .............. A61B 17/115 227/175.1 |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |

(56) References Cited

U.S. PATENT DOCUMENTS

| | | |
|---|---|---|
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 * | 10/2008 | Milliman ............. A61B 17/068 227/178.1 |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 * | 4/2009 | Aranyi ................ A61B 17/072 227/176.1 |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 * | 9/2010 | Milliman ............ A61B 17/1114 227/175.1 |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |

(56) References Cited

U.S. PATENT DOCUMENTS

| | | | |
|---|---|---|---|
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 * | 7/2011 | Milliman | A61B 17/1155 227/175.1 |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 * | 9/2011 | Milliman | A61B 17/115 227/175.1 |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,496,157 B2 | 7/2013 | Olson |
| 2003/0111507 A1 | 6/2003 | Nunez |
| 2004/0195289 A1 * | 10/2004 | Aranyi | A61B 17/072 227/180.1 |
| 2005/0051597 A1 | 3/2005 | Toledano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2005/0205639 A1 * | 9/2005 | Milliman | A61B 17/115 227/175.1 |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0144897 A1 | 7/2006 | Jankowski et al. |
| 2006/0201989 A1 | 9/2006 | Ojeda |
| 2006/0241692 A1 | 10/2006 | McGuckin et al. |
| 2006/0271104 A1 | 11/2006 | Viola et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0230581 A1 * | 9/2008 | Marczyk | A61B 17/115 227/176.1 |
| 2009/0230170 A1 * | 9/2009 | Milliman | A61B 17/0686 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 * | 2/2010 | Milliman | A61B 17/1114 227/175.1 |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 * | 5/2010 | Hessler | A61B 17/1114 227/179.1 |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 * | 12/2010 | Milliman | A61B 17/1114 227/175.1 |
| 2011/0006100 A1 * | 1/2011 | Milliam | A61B 17/115 227/175.2 |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 * | 2/2011 | Milliman | A61B 17/115 227/180.1 |
| 2011/0057016 A1 | 3/2011 | Bettuchi |
| 2011/0089219 A1 * | 4/2011 | Hessler | A61B 17/115 227/175.1 |
| 2011/0095067 A1 | 4/2011 | Ohdaira |
| 2011/0095068 A1 | 4/2011 | Patel |
| 2011/0095069 A1 * | 4/2011 | Patel | A61B 17/115 227/180.1 |
| 2011/0095070 A1 | 4/2011 | Patel et al. |
| 2011/0101065 A1 * | 5/2011 | Milliman | A61B 17/068 227/175.1 |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |

FOREIGN PATENT DOCUMENTS

| | | | |
|---|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2100561 A2 | 9/2009 |
| EP | 2153781 A2 | 2/2010 |
| EP | 2258282 A2 | 12/2010 |
| EP | 2545859 A1 | 1/2013 |
| EP | 2586384 A1 | 5/2013 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |

(56) References Cited

FOREIGN PATENT DOCUMENTS

WO         2001/054594 A1     8/2001
WO         2008/107918 A1     9/2008

OTHER PUBLICATIONS

Chinese Office Action dated Jun. 22, 2017, issued in CN Application No. 201410261530.
European Search Report dated Sep. 23, 2014 issued by the European Patent Office in corresponding European Patent Application No. 14 17 1894 (8 pgs.).
EP OA dated Nov. 3, 2015, issued in EP Appln. No. 14 171 894.
Japanese Office Action dated Oct. 19, 2018 issued in JP Application No. 201410261530.
Chinese Office dated Jun. 3, 2019, issued in CN Appln No. 201410261530.

\* cited by examiner

EEA ANVIL SNAP RING ACTIVATOR

CROSS-REFERENCE TO RELATED APPLICATIONS

This application is a Continuation of U.S. patent application Ser. No. 13/915,953 filed Jun. 12, 2013, and the disclosure of the above-identified application is hereby incorporated by reference in its entirety.

BACKGROUND

1. Technical Field

The present disclosure relates generally to a surgical fastening device for applying surgical fasteners to body tissue. More particularly, the present disclosure relates to a surgical fastening device suitable for performing circular anastomosis and/or treatment to internal walls of hollow tissue organs.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a fastener instrument which drives a circular array of fasteners, e.g., staples, through the end section of each organ section and simultaneously cores any tissue interior of the driven circular array of staples to free the tubular passage. Examples of instruments for performing circular anastomosis of hollow organs are described in U.S. Pat. Nos. 6,053,390; 5,588,579; 5,119,983; 5,005,749; 4,646,745; 4,576,167; and 4,473,077, each of which is incorporated herein in its entirety by reference. Typically, these instruments include an elongated shaft having a handle portion at a proximal end to actuate the instrument and a fastener holding component disposed at a distal end. An anvil assembly including an anvil rod with attached anvil head is mounted to the distal end of the instrument adjacent the fastener holding component. Opposed end portions of tissue of the hollow organ(s) to be fastened are clamped between the anvil head and the fastener holding component. The clamped tissue is joined by driving one or more fasteners from the fastener holding component so that the ends of the fasteners pass through the tissue and are deformed by the anvil head. An annular knife is concurrently advanced to core tissue of the hollow organ to free a tubular passage within the organ.

In many surgical fastening devices for anastomosis procedures, the anvil assembly is configured such that the anvil head tilts or pivots relative to the anvil rod after a firing of the surgical fastening device to facilitate, e.g., removal or advancement of the surgical fastening device through tissue by presenting a smaller cross-sectional profile. However, given the close tolerances of the movable components of such a surgical fastening device, various movable components may interfere with the pivoting or tilting of the anvil head with respect to the anvil rod. Further, tissue surrounding the point of connection of the anvil head and anvil rod may interfere with the pivoting or tilting of the anvil head with respect to the anvil rod.

Accordingly, it would be desirable to provide a surgical fastening apparatus that is configured to secure components of the surgical fastening apparatus such that an anvil head may pivot freely with respect to an anvil rod. It would further be desirable to provide a surgical fastening apparatus configured to maintain tissue spaced away from the point of connection of an anvil rod and anvil head such that the anvil head may tilt or pivot freely with respect to the anvil rod.

SUMMARY

According to one aspect of the present disclosure, a surgical fastening apparatus is disclosed. The surgical fastening apparatus includes a handle assembly, a central body portion extending from the handle assembly, and a distal head portion. The distal head portion includes a shell assembly and an anvil assembly. The anvil assembly includes an anvil head assembly and an anvil center rod assembly. The anvil head assembly includes an anvil head defining an interior recess, an activator plate, a deformable member, and a securing member. The interior recess supports the activator plate, the deformable member is positioned distally of the activator plate, and the securing member is positioned proximally of the activator plate. The anvil center rod assembly defines a longitudinal axis and is pivotably connected to the anvil head assembly about a pivot axis. The anvil center rod assembly includes a plunger in mechanical communication with the anvil head. The plunger is configured to contact the anvil head assembly upon an actuation of the surgical fastening apparatus. Upon the actuation of the surgical fastening apparatus, the deformable member is configured to deform such that the activator plate is advanced distally into the interior recess to facilitate the anvil head pivoting about the pivot axis.

According to one aspect of the present disclosure, the anvil head includes a post extending proximally therefrom. According to another aspect of the present disclosure, the post may define an annular groove configured to securely receive the securing member. According to a further aspect of the present disclosure, the post may define an aperture therethrough, the aperture configured to align with a throughbore of the anvil center rod assembly. The aperture and the throughbore are configured to receive a pivot member therethrough to pivotably attach the anvil center rod assembly with the anvil head assembly.

In one aspect of the present disclosure, the deformable member includes a body and an extension extending therefrom. The extension may be configured to deform with respect to the body.

According to another aspect of the present disclosure, the pivot axis is transverse to the longitudinal axis. In another aspect of the present disclosure, the plunger is configured to engage the anvil head assembly at a location offset from the longitudinal axis. In yet another aspect of the present disclosure, the anvil head assembly includes a cut ring disposed in the interior recess. The cut ring may be configured to receive an annular knife upon the actuation of the surgical fastening apparatus.

In another aspect of the present disclosure, the anvil center rod assembly defines a ridge configured to inhibit the anvil head from pivoting about the pivot axis. In one aspect of the present disclosure, the ridge is configured to engage a lug extending from the activation plate. In another aspect of the present disclosure, upon the actuation of the surgical fastening apparatus, the lug may be configured to move away from the ridge to facilitate pivoting of the anvil head about the pivot axis.

According to another aspect of the present disclosure, the anvil center rod assembly includes a sleeve slidably disposed thereon. The sleeve may be configured to engage tissue. Further, the sleeve may be configured to slide proximally upon pivoting of the anvil head about the pivot axis.

According to another aspect of the present disclosure, a method of using a surgical fastening apparatus is disclosed, and includes providing an anvil center rod assembly and an anvil head assembly pivotably attached thereto. The method also includes actuating the surgical fastening apparatus such that an annular knife contacts a cut ring within the anvil head assembly. The method further includes advancing the annular knife distally such that the cut ring moves an activation plate and a deformable member distally of the cut ring, the deformable member having a body and an extension configured to deform relative to the body. The method also includes securing the activation plate with a securing ring such that the anvil head assembly pivots relative to the anvil center rod assembly. According to another aspect of the present disclosure, the method may also include pivoting the anvil head assembly relative to the anvil center rod assembly such that a smaller cross-sectional profile of the surgical fastening apparatus is created.

BRIEF DESCRIPTION OF THE DRAWINGS

Various embodiment of the presently disclosed surgical stapling device are disclosed herein with reference to the drawings, wherein.

DETAILED DESCRIPTION

With reference now to the drawings wherein like numerals represent like elements throughout the several views, the presently-disclosed surgical fastening apparatus will be described. As used herein, the term "operator" may refer to any user, e.g., a nurse, doctor, or clinician, of the presently-disclosed surgical fastening apparatus. Further, the term "distal" refers to that portion of the surgical fastening apparatus, or component thereof, further from the operator while the term "proximal" refers to that portion of the surgical fastening apparatus, or component thereof, closer to the operator.

Figure 1:
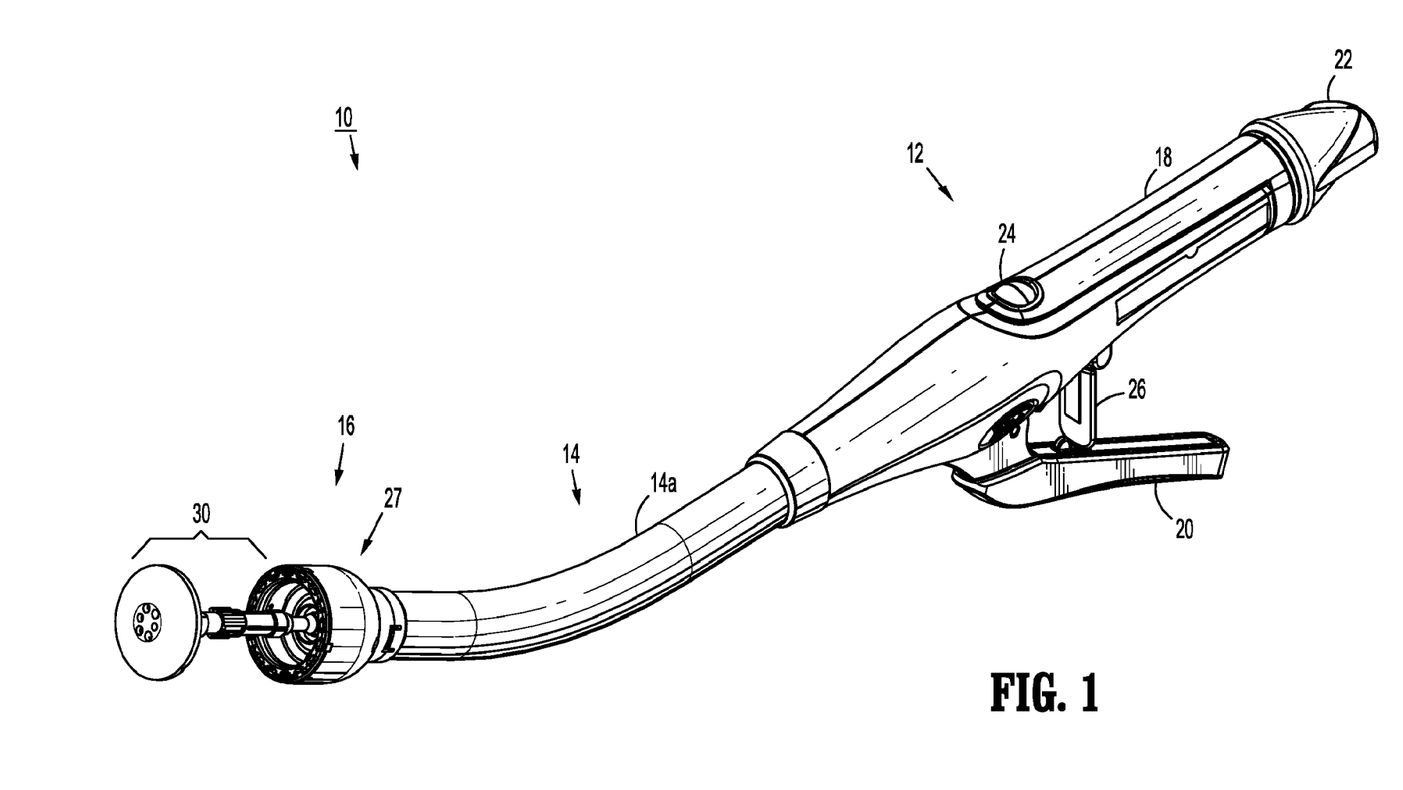
FIG. 1 is a perspective view of a surgical fastening apparatus according to the present disclosure.
Figure 2:
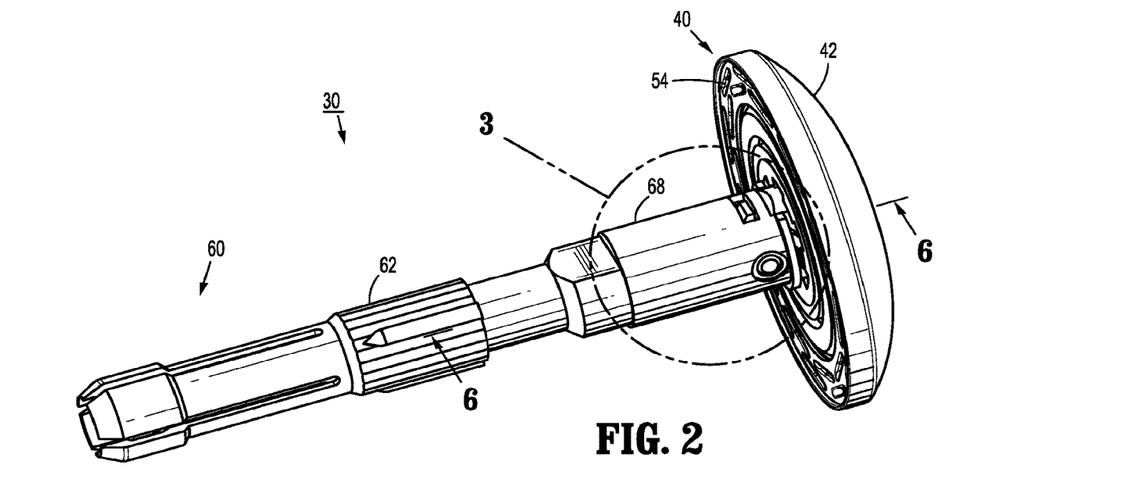
FIG. 2 is a perspective view of an anvil assembly of the surgical fastening apparatus shown in FIG. 1.
Figure 3:
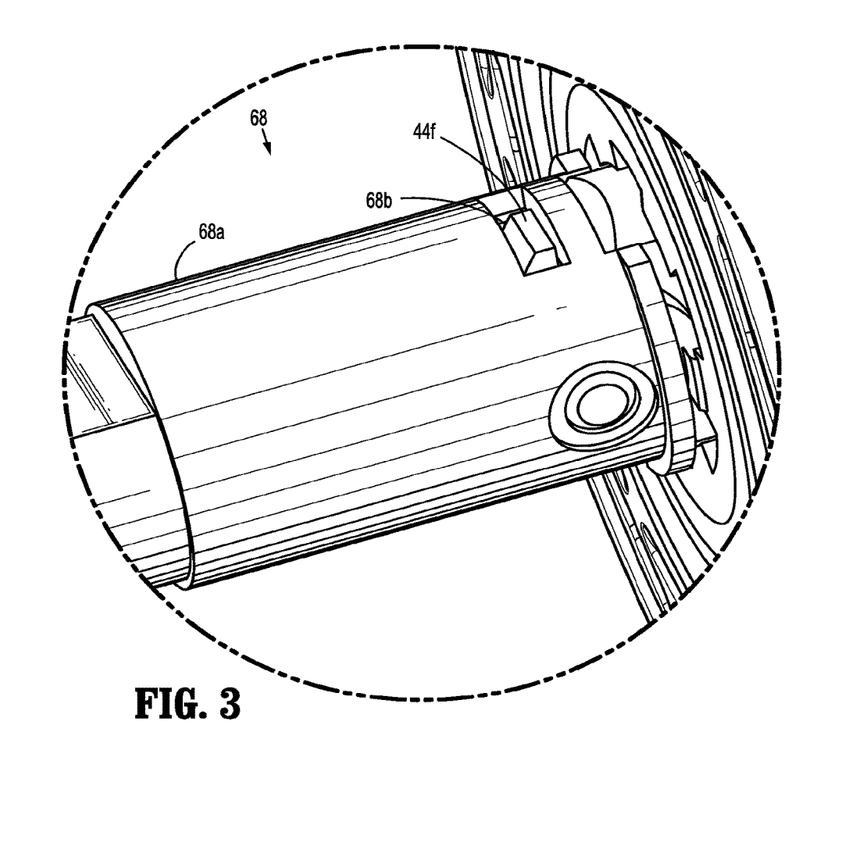
FIG. 3 is an enlarged view of the area of detail identified in FIG. 2.
Figure 4:
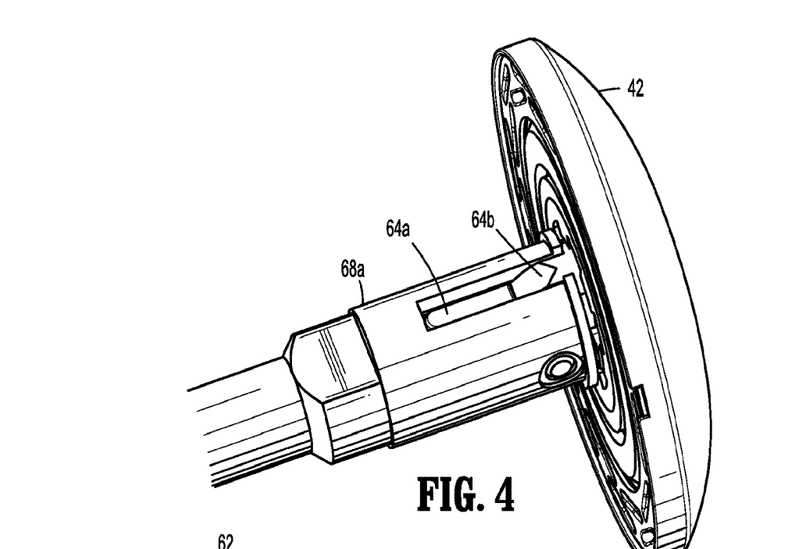
FIG. 4 is a perspective view of the distal portion of the anvil assembly shown in FIG. 2.
Figure 5:
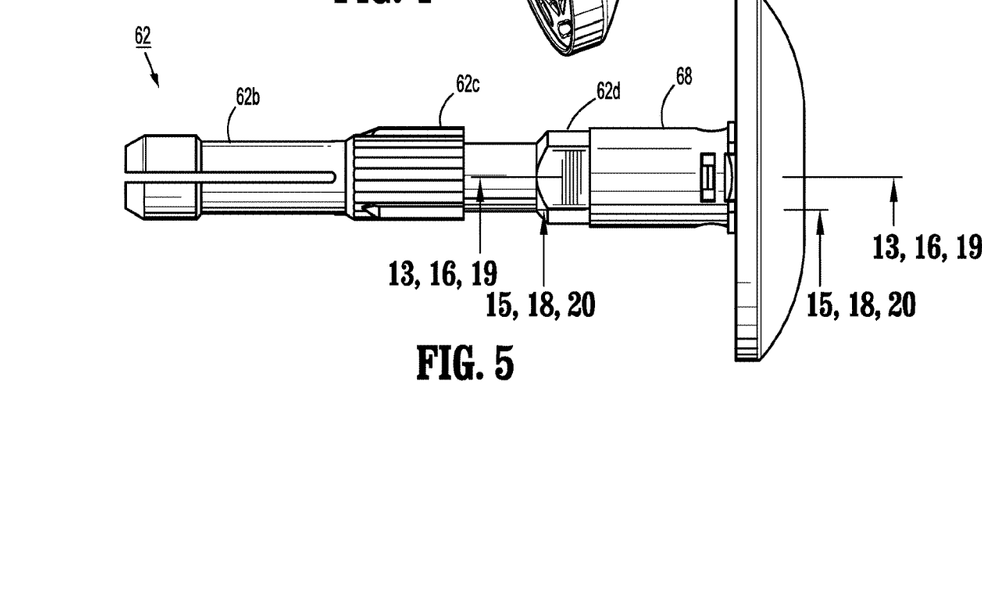
FIG. 5 is a side view of the anvil assembly shown in FIG. 2.
Figure 6:
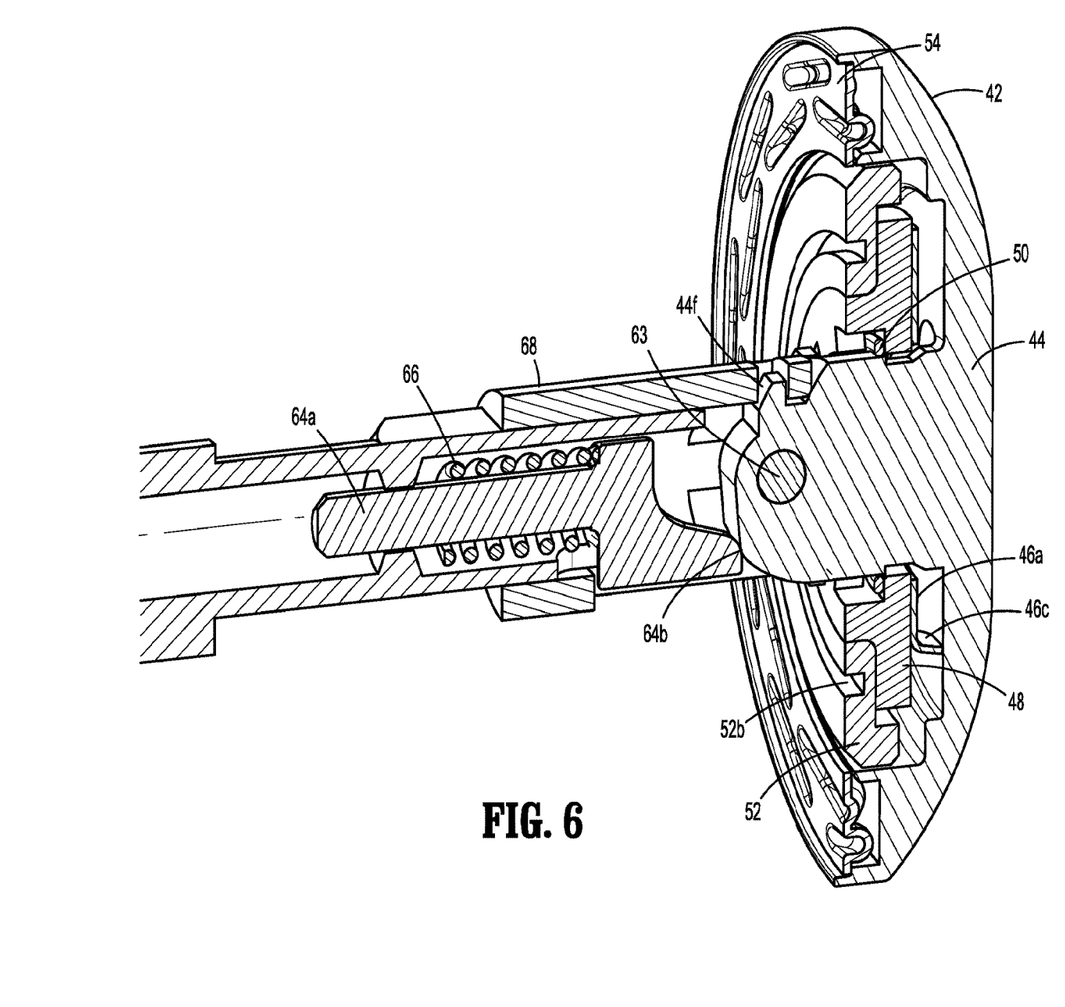
FIG. 6 is a cross-sectional view taken along section line 6-6 of FIG. 2.

Referring initially to FIG. 1, an embodiment of the presently disclosed surgical fastening apparatus is illustrated generally as 10. Briefly, surgical fastening apparatus 10 includes a proximal handle assembly 12, an elongated central body portion 14 including a curved elongated outer tube 14a, and a distal head portion 16. Distal head portion 16 includes a shell assembly 27 and an anvil assembly 30, as will be described further below. In some embodiments, the length, shape and/or the diameter of body portion 14 and head portion 16 may also be varied to suit a particular surgical procedure.

Handle assembly 12 includes a stationary handle 18, a firing trigger 20, a rotatable approximation knob 22 and an indicator 24. Stationary handle 18 may be formed from separate handle sections (not shown), which together define a housing for the internal components of surgical fastening apparatus 10. A pivotally mounted trigger lock 26 is fastened to handle assembly 12 and is manually positioned to prevent inadvertent firing or actuation of surgical fastening apparatus 10. Indicator 24 is positioned on the stationary handle 18 and includes indicia, e.g., color coding, alpha-numeric labeling, etc., to identify to an operator whether the surgical fastening apparatus 10 has been fired or actuated and/or when the surgical fastening apparatus 10 is ready to be fired.

Figures 7, 8:
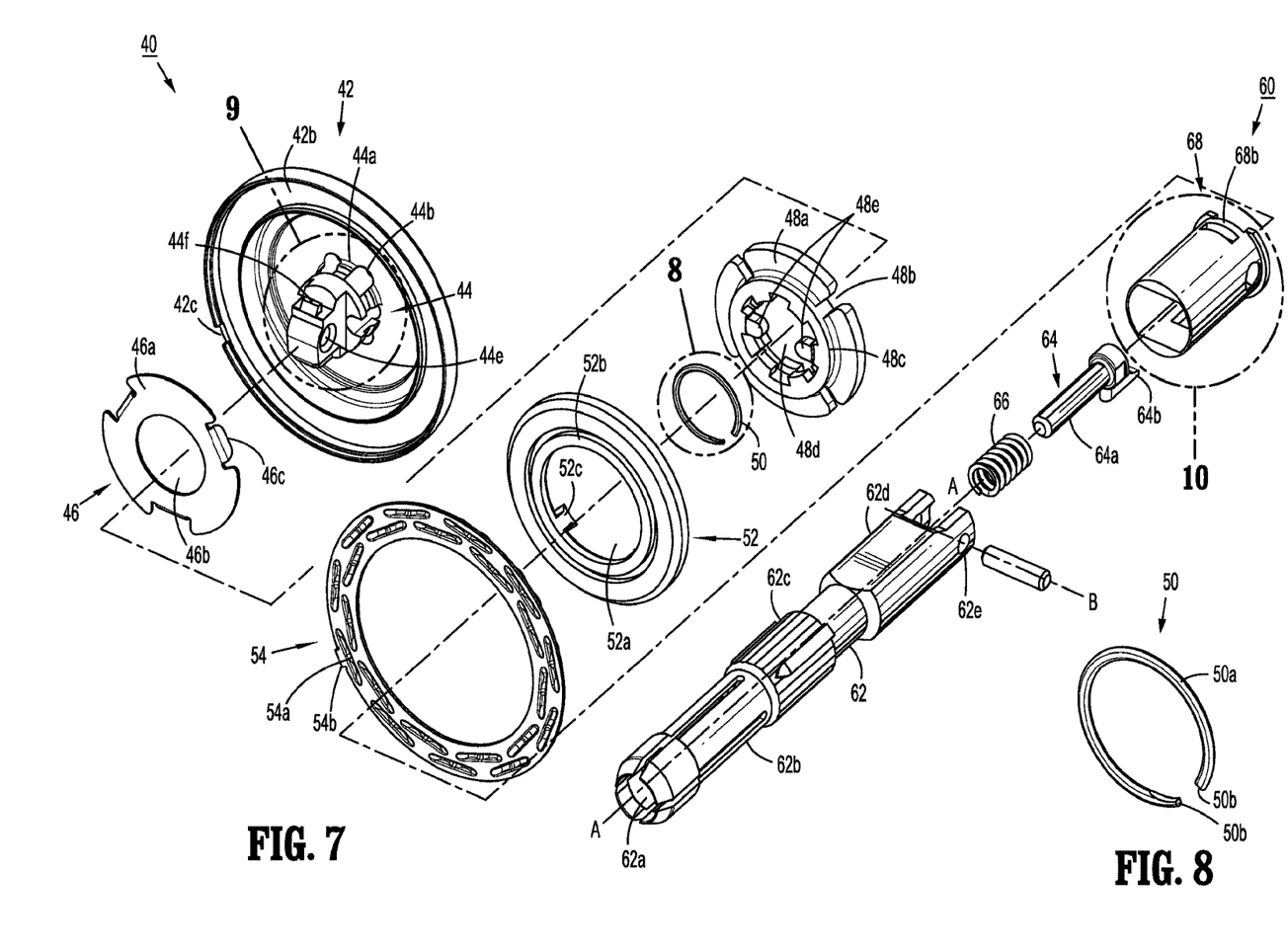
FIG. 7 is a parts-separated view of the anvil assembly shown in FIG. 2.
FIG. 8 is an enlarged view of the area of detail identified in FIG. 7.

Referring to FIGS. 2-12, anvil assembly 30 includes an anvil head assembly 40 and an anvil center rod assembly 60 (best shown in FIG. 7). Anvil head assembly 40 is pivotably coupled with anvil center rod assembly 60, as will be described further below. Anvil head assembly 40 includes, from distal to proximal, an anvil head 42, a deformable member 46, an activation plate 48, a securing ring 50, a cut ring 52, and an anvil 54.

Anvil head 42 defines a curvate outer surface and an interior recess 42a defined by the curvate outer surface. An outer annular ledge 42b is defined along the outer periphery of the interior recess 42a. A post 44 is centrally positioned within the interior recess 42a defined by the anvil head 42. Post 44 protrudes proximally from the interior recess 42a defined by the anvil head 42 and defines a base 44a having a pair of notches 44b formed radially inwardly thereon, and an annular groove 44c formed therearound. Annular groove 44c is located proximally above the notches 44b in the base 44a of post 44. Post 44 also includes a coupling portion 44d having an aperture 44e therethrough and a tooth 44f extending therefrom for coupling with the anvil center rod assembly 60, as will be described further below.

Figure 9:
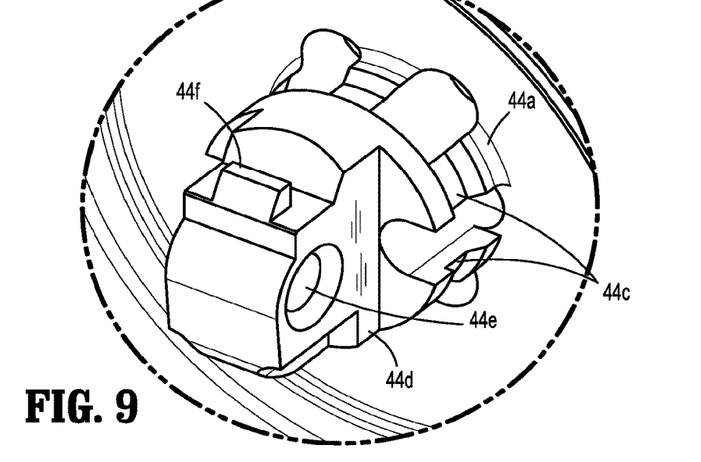
FIG. 9 is an enlarged view of the area of detail identified in FIG. 7.

Deformable member 46 includes a body 46a having a substantially annular configuration and defining a central opening 46b therethrough. One or more extensions 46c protrude radially outward and distally from the body 46a, and are configured for movement relative to the body 46a. Accordingly, extensions 46c may be formed of a different material than body 46a, e.g., a material with different (greater or lesser) flexibility, or may be pivotably attached to body 46a, e.g., via a living hinge. Deformable member 46 is configured to sit within the interior recess 42a of anvil head 42, with the extensions 46c contacting the distal surface of the interior recess 42a and spacing the body 46a thereabove.

Activation plate 48 is configured for disposition within the interior recess 42a of anvil head 42 proximally abutting the body 46a of deformable member 46. Activation plate 48 includes a substantially circular base portion 48a which defines one or more cutouts 48b formed along an outer periphery thereof. A raised platform 48c protrudes proximally from the base portion 48a of the activation plate 48, and defines a central opening 48d which is positioned about post 44 within the interior recess 42a of anvil head 42 between post 44 and annular outer ledge 42b. A pair of diametrically opposed lugs 48e extends radially inwardly into central opening 48d. Lugs 48e engage a portion of anvil center rod assembly 60, as will be described further below.

Securing ring 50 has a body 50a having substantially annular configuration and may include a discontinuity in its outer circumference. The discontinuity in the outer circumference of securing ring 50 may defined by a pair of tapered ends 50b of the body 50a. Securing ring 50a is configured to sit proximally above the activation plate 48, and is configured to engage the annular groove 44c of the post 44 of anvil head 42, as will be described further below.

Cut ring 52 has a substantially circular configuration and defines an opening 52a having a larger diameter but substantially similar configuration as the outer circumference of the raised platform 48c of activation plate 48. In this manner, cut ring 52 is configured to fit over the raised platform 48c of activation plate 48 to concentrically and radially fix cut ring 52 on activation plate 48. Cut ring 52 defines an annular groove 52b positioned radially between the outer circumference of the cut ring 52 and the opening 52a. A tab 52c protrudes distally from the cut ring 52 and is configured to align with one of the cutouts 48b formed in the base portion 48a of the activation plate 48 to concentrically and radially fix the cut ring 52 about the activator plate 48 such that relative rotational movement between the cut ring 52 and activation plate 48 is inhibited. In one embodiment, cut ring 52 is formed from polyethylene and is fixedly secured to activation plate 48 using, for example, an adhesive. Activation plate 48 may be formed from a different, e.g., harder material such as a metal. Alternately other materials of construction may be used to construct activation plate 48 and cut ring 52. Cut ring 52 and activation plate 48 are slidably mounted about post 44.

Anvil 54 is a substantially annular member configured to be supported on the outer annular ledge 42b of anvil head 42 and includes a plurality of pockets 54a for receiving and deforming surgical fasteners, e.g., surgical staples (not shown). At least one tab 54b extends radially outwardly from anvil 54 and is dimensioned to be received within a cutout 42c formed along the outer periphery of anvil head 42. Tab 54b and cutout 44c interengage to align anvil 54 within outer annular ledge 44b of anvil head 42 and to inhibit rotation of anvil 52 with respect to anvil head 42 and vice versa.

Figure 12:
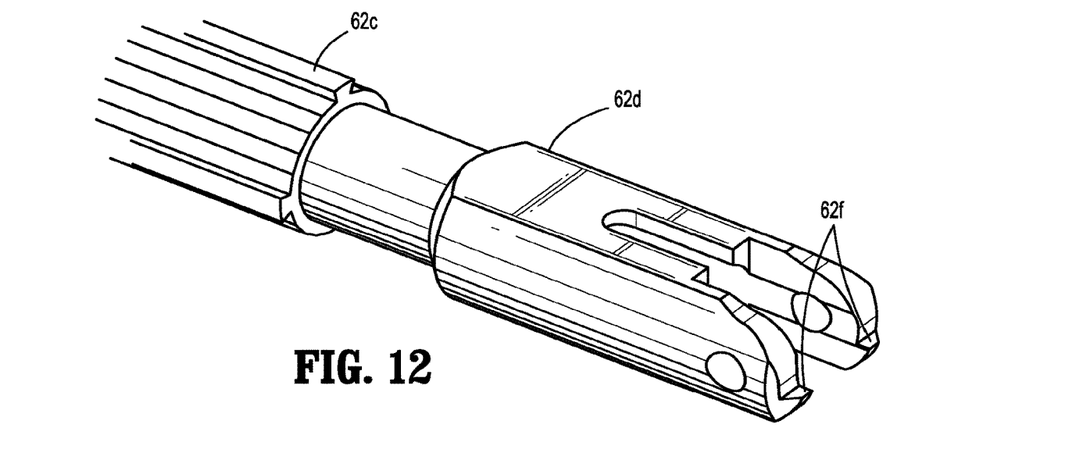
FIG. 12 is a perspective view of the distal portion of the anvil center rod shown in FIG. 7.

Anvil center rod assembly 60 includes anvil center rod 62, a pivot member 63, a plunger 64, a plunger spring 66, and a sleeve 68. Anvil center rod 62 is a substantially elongate, cylindrical member defining a longitudinal axis "A" and a lumen 62a extending therethrough. Anvil center rod 62 defines a proximal portion 62b, a central portion 62c, and a distal portion 62d. The distal portion 62d of anvil center rod 62 defines a transverse throughbore 62e, which is extends through the distal portion 62d transverse to and laterally spaced from the longitudinal axis "A". The aperture 44e of the post 44 of anvil head 42 aligns with the throughbore 62e to receive a pivot member 63 therethrough. Pivot member 63 is a cylindrical member configured for insertion through the throughbore 62e of anvil center rod 62 and aperture 44e of post 44 and defines a pivot axis "B" such that the anvil head 42 may pivot about pivot axis "B" relative to anvil center rod 62. Pivot axis "B" may be transverse to longitudinal axis "A." Accordingly, pivot member 63 may be formed of a rigid material configured to withstand torsional and/or axial loading, e.g., metal or composite.

Plunger 64 is a substantially elongate member slidably positioned in the lumen 62a formed axially through the center rod 62. Plunger 64 includes a body 64a and an engagement finger 64b protruding distally from the body. Engagement finger 64b is offset from the pivot axis "B" of anvil head 42 and biased into engagement with the base portion 44a of post 44 by plunger spring 66. Plunger spring 66 is compressibly disposed in the lumen 62a of center rod 62a proximally abutting the plunger 64 such that the plunger spring 66 maintains a consistent distal bias against the plunger spring 66. Because the engagement finger 64b of the plunger 64 contacts the post 44 at a location laterally spaced from the longitudinal axis "A," the portion of the post 44 between the point of contact of plunger 64 and the pivot axis "B" acts as a moment arm such that the anvil head 42 is normally biased to pivot or tilt relative to the anvil center rod 62 about the pivot axis "B."

Figure 10:
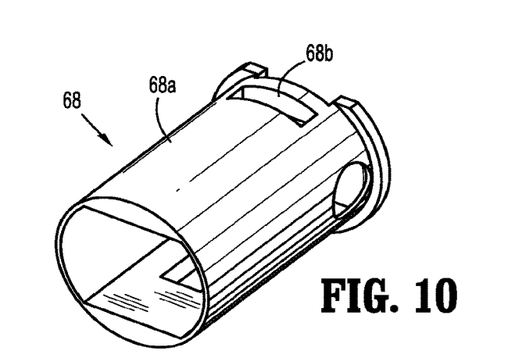
FIG. 10 is a perspective view of a sleeve of the anvil assembly shown in FIG. 7.
Figure 11:
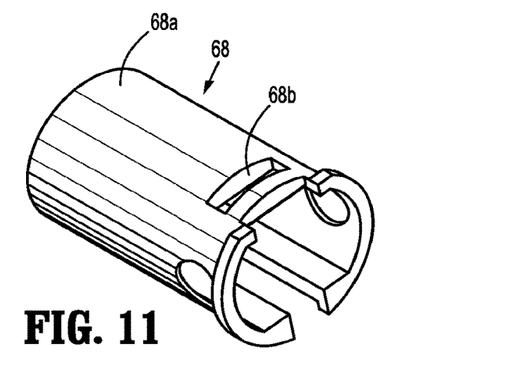
FIG. 11 is another perspective view of the sleeve shown in FIG. 10.

Sleeve 68 is a substantially cylindrical member having a body 68a defining an aperture 68b toward a distal end thereof. Sleeve 68 is slidably disposed along the outer surface about the anvil center rod 62. In a pre-fired or unactuated position, sleeve 68 is disposed about the distal portion 62d of the anvil center rod 62 such that the tooth 44f of the post 44 of anvil head 42 protrudes through the aperture 68b of the sleeve 68. In this manner, sleeve 68 fixes the anvil center rod assembly 60 and anvil head assembly 40 in the unactuated position. Sleeve 68 is configured to engage and move tissue during operation of the surgical fastening apparatus 10, as will be described further below.

In a pre-fired or unactuated position, lugs 48e formed on activation plate 48 engage a respective pair of ridges 62f protruding distally from the distal portion 62d of anvil center rod 62. In this manner, the interengagement of lugs 48e with ridges 62f of anvil center rod 62 inhibits the anvil head 42 from pivoting with respect to the anvil center rod 62. Accordingly, lugs 48e function to lock the anvil head 42 in the unactuated or pre-fired position. The interengagement of sleeve 68 and post 44 of anvil head 42 as described above also functions to lock the anvil head 42 in the pre-fired or unactuated position.

It will be understood that the various components of surgical apparatus 10 described herein may be formed of any suitable material for their intended purposes, e.g., metal, composite, and/or polymeric materials.

Figure 13:
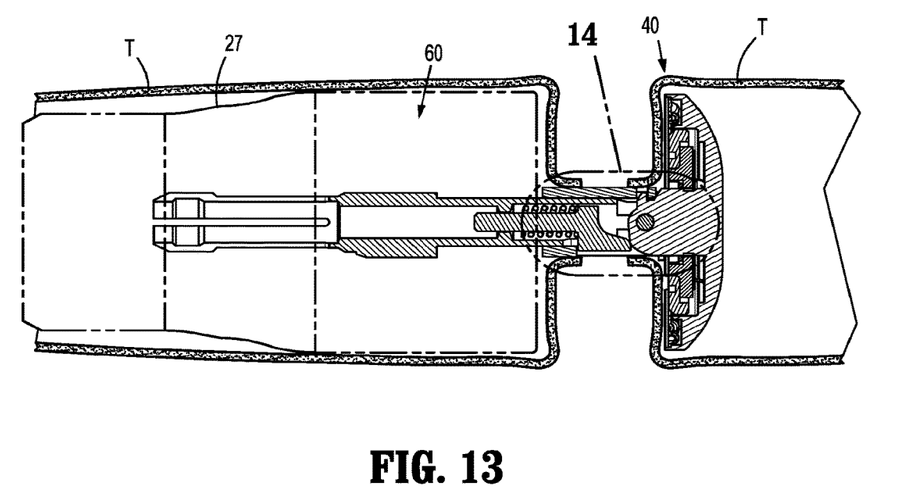
FIG. 13 is a cross-sectional view taken along section line 13-13 of FIG. 5, inserted into and engaged with tissue.
Figure 14:
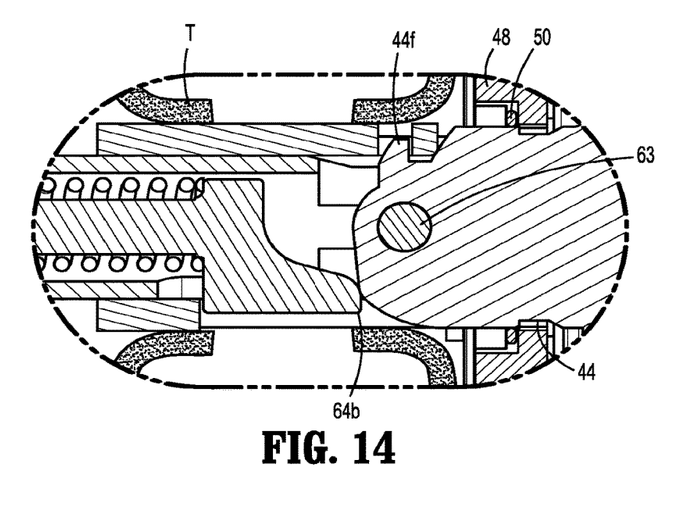
FIG. 14 is an enlarged view of the area of detail identified in FIG. 13.
Figure 15:
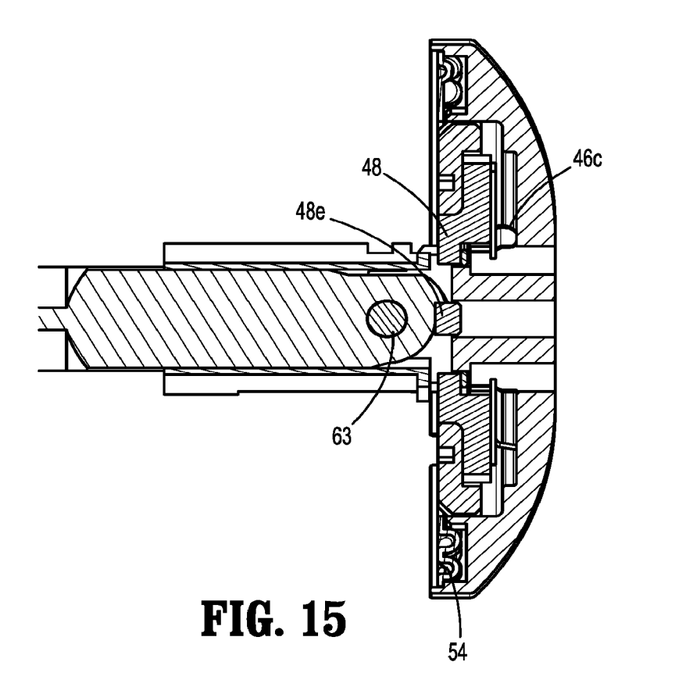
FIG. 15 is a cross-sectional view taken along section line 15-15 of FIG. 5.
Figure 16:
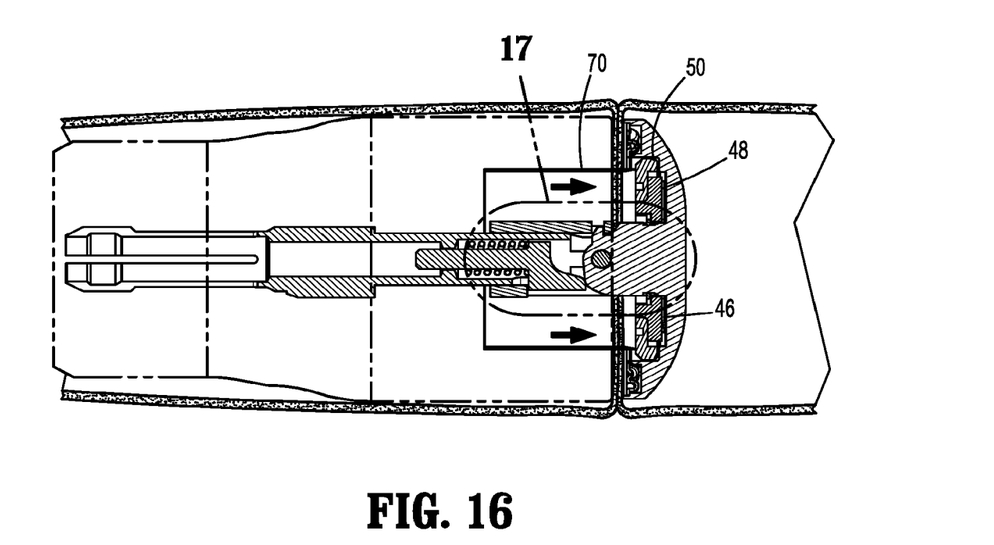
FIG. 16 is a cross-sectional view taken along section line 16-16 of FIG. 5, inserted into and engaged with tissue.
Figure 17:
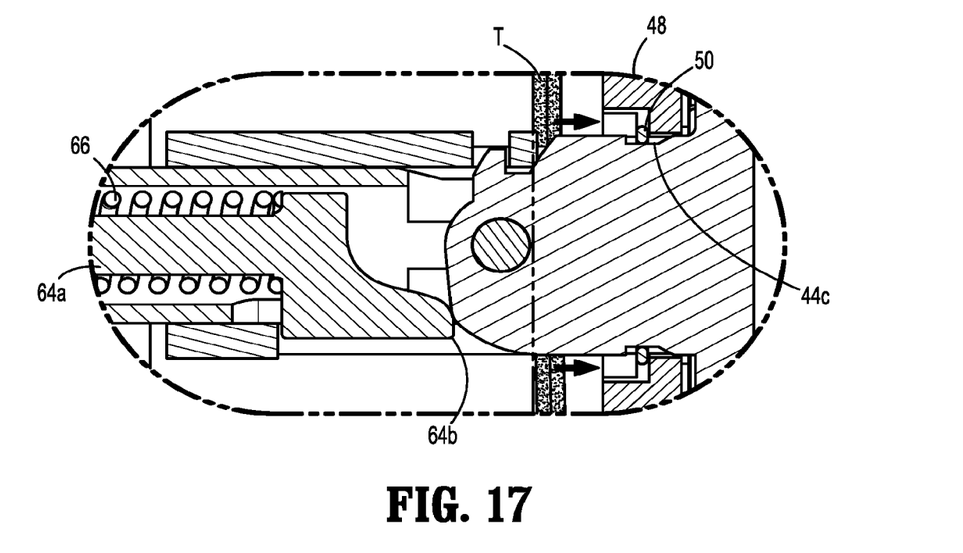
FIG. 17 is an enlarged view of the area of detail identified in FIG. 17.

Referring now to FIGS. 13, 14, and 16, surgical fastening apparatus 10 may be inserted into a body cavity, e.g., through an incision or a naturally-occurring orifice such that the distal head portion 16 of surgical fastening apparatus 10 is positioned to engage adjacent sections of tissue T. The distal head portion 16 of surgical fastening apparatus 10 is positioned such that adjacent sections of tissue T are disposed between the shell assembly 27 and the anvil head assembly 40, with the anvil center rod assembly 60 extending therebetween. An operator may then rotate approximation knob 22 (FIG. 1) to approximate anvil head assembly 40 toward shell assembly 27. An operator may then engage firing trigger 20 (FIG. 1) to effect one or more firing strokes of surgical fastener apparatus 10. Upon a firing stroke of the surgical fastening apparatus 10, a plurality of fasteners, e.g., staples (not shown), are ejected from shell assembly 27 into the pockets 54a anvil 54. Upon another firing stroke of the surgical fastening apparatus 10, an annular knife 70 (shown in phantom) is advanced distally through tissue T and into the annular groove 52c of cut ring 52. Cut ring 52 is accordingly forced distally against the activation plate 48, which causes the deformable member 46 to deform. Specifically, the extensions 46c of the deformable member 46 are caused to deform, i.e., extensions 46c bend, fold, crush, and/or flex such that the body 46b of deformable member 46, and the activation plate 48 and securing ring 50 disposed thereabove, shift deeper distally into the interior recess 42a of anvil head 42.

As the securing ring 50 moves distally, the body 50a of securing ring 50 engages the annular groove 44c of post 44 of anvil head 50. Securing ring 50 is configured to "snap" or otherwise lock into annular groove 44c such that securing ring 50 remains substantially axially stationary about post 44. Tapered ends 50b of securing ring 50 may aid in the transition of the securing ring 50 into the annular groove 44c. As the body 50a of securing ring 50 protrudes radially outward from the annular groove 44c of post 44, the body 50a maintains the activation plate 48 at a location distally of the annular groove 44c along post 44.

Figure 18:
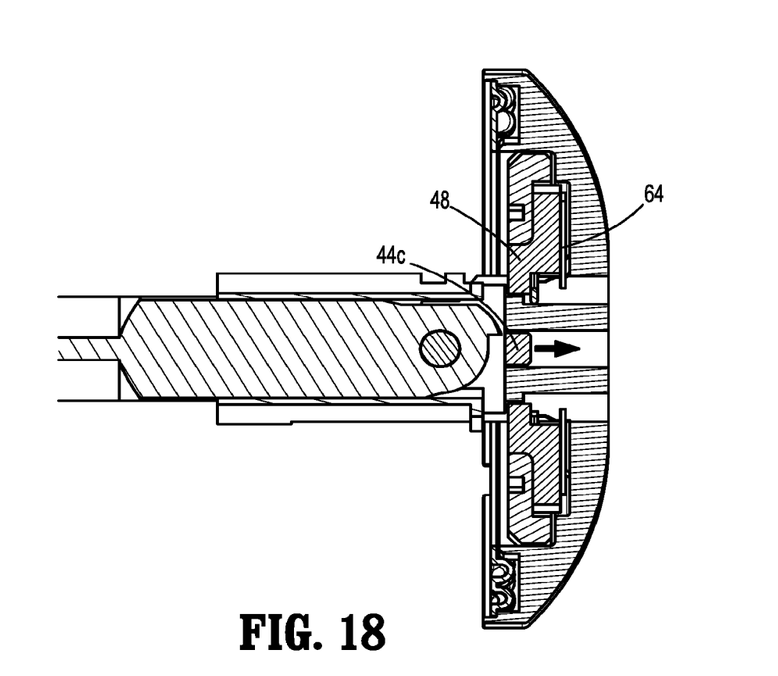
FIG. 18 is a cross-sectional view taken along section line 18-18 of FIG. 5, after a firing of the surgical fastening apparatus shown in FIG. 1.
Figure 19:
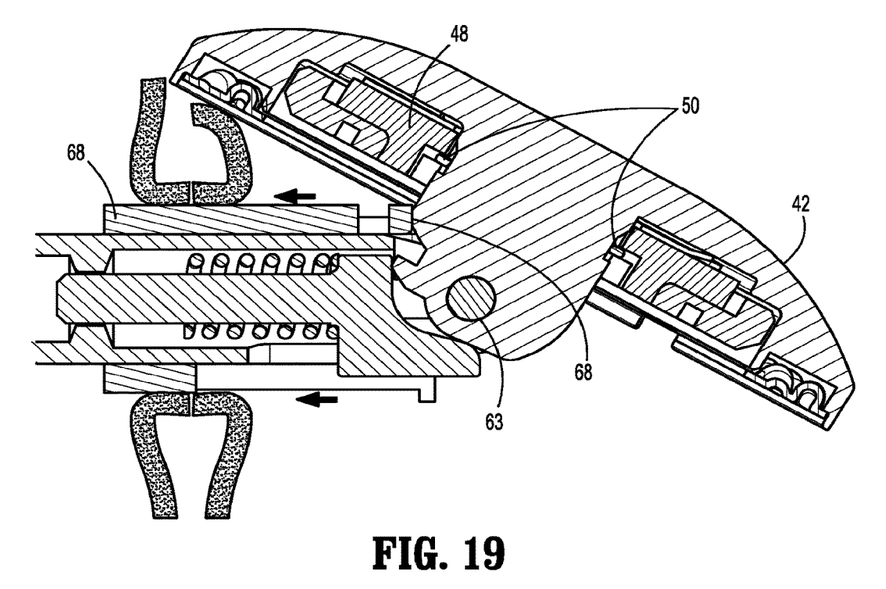
FIG. 19 is a cross-sectional view taken along section line 19-19 of FIG. 5, inserted into and engaged with tissue, and with the anvil head being tilted relative to an anvil center rod.
Figure 20:
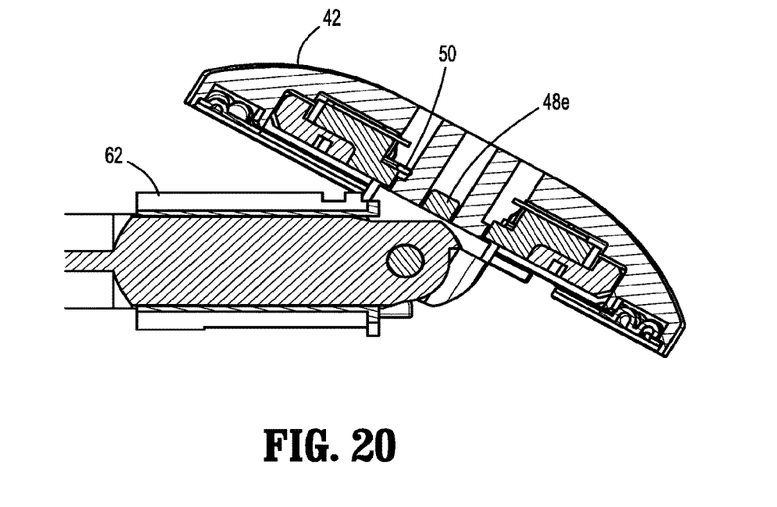
FIG. 20 is a cross-sectional view taken along section line 20-20 of FIG. 5, with the anvil head being tilted relative to an anvil center rod.

Further, as the activation plate 48 moves distally, the lugs 48e of activation plate 48 disengage from the ridges 62f of anvil center rod 62 such that anvil head 42 is free to pivot or tilt relative to anvil center rod 62 under the spring bias of plunger spring 64. As the anvil head 42 pivots about the pivot axis "B," the tooth 44f of post 44 swings radially inward and disengages from the aperture 68e of sleeve 68. Accordingly, as one side of the anvil head 42 pivots or tilts proximally, the anvil head 42 engages the sleeve 68 and cams the sleeve 68 proximally along the anvil center rod 62.

Because the activation plate 48 is maintained distally below the annular groove 44c of post 44, the lugs 48e of activation plate 48e remain spaced from the ridges 62f of anvil center rod 62. In this manner, the securing ring 50 functions to inhibit the activation plate 48 from undesirably migrating proximally such that the lugs 48e of activation plate 48 re-engage ridges 62f of the anvil center rod 62. Further, because the sleeve 68 is engaged with surrounding tissue "T," proximal movement of the sleeve 68 carries tissue "T" disposed thereon proximally. In this manner, tissue T is carried away from the pivot axis "B" during tilting of the anvil head 42 such that tilting of the anvil head 42 relative to the anvil center rod 62 is uninhibited by tissue "T." Thus, surgical fastening apparatus 10 is configured such that anvil head 42 tilts uninhibited through a maximum degree of pivoting such that the transverse profile of surgical fastening apparatus 10 is reduced, e.g., for removal through an incision or naturally-occurring orifice or for advancement through a body cavity.

It will be understood that various modifications may be made to the embodiments disclosed herein. Therefore, the above description should not be construed as limiting, but merely as exemplifications of disclosed embodiments. Those skilled in the art will envision other modifications within the scope and spirit of the claims appended hereto.

The invention claimed is:

1. An anvil assembly for use with a surgical fastener apparatus having a handle configured to move through at least one firing stroke to deliver fasteners, the anvil assembly comprising:
   an anvil center rod configured for coupling with the surgical fastener apparatus and defining a longitudinal axis;
   an anvil head mounted to the anvil center rod, the anvil head including a post and configured for pivotal movement relative to the anvil center rod between an initial condition and a pivoted condition;
   an activation portion defining a central opening and being configured to engage the anvil center rod to secure the anvil head in the initial condition, the activation portion configured for longitudinal movement from an initial position to an advanced position upon movement of the handle through the at least one firing stroke to release the anvil head to permit pivotal movement to the pivoted condition;
   a deformable portion supported with the anvil head adjacent the activation portion, the deformable portion configured to deform during the at least at least one firing stroke to permit longitudinal movement of the activation portion to the advanced position; and
   a securing portion supported within the central opening of the activation portion and extending around the post, the securing portion movable in relation to the activation portion and positioned to directly engage the post to secure the activation portion in the advanced position when the anvil head is in the initial condition.

2. The anvil assembly according to claim 1 wherein the activation portion is configured to engage the deformable portion upon longitudinal movement to the advanced position to cause deformation of the deformable portion.

3. The anvil assembly according to claim 2 wherein the securing portion is configured to advance during longitudinal movement of the activation portion.

4. The anvil assembly according to claim 3 wherein the securing portion is configured to securely engage the post upon movement of the activation portion to the advanced position.

5. The anvil assembly according to claim 4 wherein the post defines an annular groove segment configured to at least partially receive the securing portion to lock the securing portion relative to the post of the anvil head.

6. The anvil assembly according to claim 3 wherein the activation portion defines at least one lug and wherein the anvil center rod defines at least one ridge, the at least one lug and the at least one ridge in cooperative engagement to retain the anvil head in the initial condition, the at least one lug and the at least one ridge releasing upon movement of the activation portion to the advanced position to permit pivotal movement of the anvil head to the pivoted condition.

7. The anvil assembly according to claim 3 wherein the anvil head defines a recess, the recess configured to accommodate the deformable portion upon deformation thereof.

8. The anvil assembly according to claim 3 wherein the anvil head is normally biased toward the pivoted condition.

9. The anvil assembly according to claim 8 wherein the anvil center rod includes a plunger in contact with the anvil head, the plunger being biased toward the anvil head whereby, upon release of the anvil head from the activation portion, the plunger drives the anvil head to the pivoted condition.

10. The anvil assembly according to claim 3 wherein the deformable portion includes a body and an extension depending from the body, the extension being configured to deform.

11. The anvil assembly according to claim 3 further including a cut ring secured to the activation portion, the cut ring advanceable during movement of the handle through the at least one firing stroke to cause corresponding movement of the activation portion toward the advanced position.

12. An anvil assembly comprising:
an anvil center rod defining a longitudinal axis;
an anvil head pivotably mounted to the anvil center rod between an initial condition and a pivoted condition, the anvil head including a post;
an activation portion supported within the anvil head for longitudinal movement from an initial position to an advanced position to permit pivotal movement of the anvil head to the pivoted condition, the activation portion in its initial position engaging the anvil center rod to secure the anvil head in the initial condition;
a deformable portion supported within the anvil head adjacent the activation portion, the deformable portion engaging the activation portion when the activation portion is in its initial position to retain the activation portion in its initial position, the deformable position configured to deform to permit longitudinal movement of the activation portion to the advanced position; and
a securing portion extending about the post and movable in relation to the activation portion during movement of the activation portion from its initial position to its advanced position, the securing portion directly engaging the post when the activation portion is in its advanced position to secure the activation portion in its advanced position.

13. The anvil assembly according to claim 12, wherein the activation portion engages the deformable portion upon longitudinal movement of the activation portion towards the advanced position to cause deformation of the deformable portion.

14. The anvil assembly according to claim 12, wherein the post defines an annular groove segment that receives the securing portion to lock the securing portion in relation to the post of the anvil head.

15. The anvil assembly according to claim 12, wherein the activation portion defines at least one lug and wherein the anvil center rod defines at least one ridge, the at least one lug and the at least one ridge in cooperative engagement to retain the anvil head in the initial condition, the at least one lug and the at least one ridge releasing upon movement of the activation portion to the advanced position to permit pivotal movement of the anvil head to the pivoted condition.

16. The anvil assembly according to claim 12, wherein the anvil head is normally biased toward the pivoted condition.

17. The anvil assembly according to claim 16, wherein the anvil center rod includes a plunger in contact with the anvil head, the plunger being biased toward the anvil head whereby, upon release of the anvil head from the activation portion, the plunger drives the anvil head to the pivoted condition.

18. The anvil assembly according to claim 12, further including a cut ring fixedly secured to the activation portion.

* * * * *